US010687724B2

(12) United States Patent
Baxi et al.

(10) Patent No.: US 10,687,724 B2
(45) Date of Patent: Jun. 23, 2020

(54) USER'S PHYSIOLOGICAL CONTEXT SENSING METHOD AND APPARATUS

(71) Applicant: Intel Corporation, Santa Clara, CA (US)

(72) Inventors: Amit S. Baxi, Thane (IN); Vincent S. Mageshkumar, Navi Mumbia (IN)

(73) Assignee: Intel Corporation, Santa Clara, CA (US)

( * ) Notice: Subject to any disclaimer, the term of this patent is extended or adjusted under 35 U.S.C. 154(b) by 829 days.

(21) Appl. No.: 14/750,083

(22) Filed: Jun. 25, 2015

(65) Prior Publication Data

US 2016/0374577 A1 Dec. 29, 2016

(51) Int. Cl.
*A61B 5/0402* (2006.01)
*A61B 5/0476* (2006.01)
(Continued)

(52) U.S. Cl.
CPC ........ *A61B 5/0402* (2013.01); *A61B 5/04012* (2013.01); *A61B 5/0476* (2013.01);
(Continued)

(58) Field of Classification Search
CPC . A61B 5/04012; A61B 5/0402; A61B 5/0476; A61B 5/117; A61B 5/6824; A61B 5/7203; A61B 5/7221; G06F 1/3231
See application file for complete search history.

(56) References Cited

U.S. PATENT DOCUMENTS

2006/0155183 A1  7/2006 Kroecker et al.
2011/0092780 A1* 4/2011 Zhang .................. A61B 5/053
                                                600/301

(Continued)

FOREIGN PATENT DOCUMENTS

JP  2007209430 A  8/2007
WO  2014043739 A1  3/2014

OTHER PUBLICATIONS

International Preliminary Report on Patentability dated Jan. 4, 2018, issued in International Application No. PCT/US2016/031068, 10 pages.

(Continued)

*Primary Examiner* — Kevin Bechtel
(74) *Attorney, Agent, or Firm* — Schwabe, Williamson & Wyatt, P.C.

(57) ABSTRACT

Embodiments of the present disclosure provide techniques and configurations for an apparatus for providing a user's physiological context measurements. In one instance, the apparatus may include a physiological context measurement module including first and second electrodes, to obtain one or more parameters of physiological context of a user in response to a provision of contact of the first and second electrodes with a portion of the user's body while the physiological context measurement module is powered on; and a third electrode coupled with the module, which may be powered on in response to detection of contact between the user's body portion and the third electrode. The first, second, and third electrodes are disposed to facilitate simultaneous contact of the user's body portion with the electrodes, and collection of the one or more parameters of the physiological context while the simultaneous contact is maintained. Other embodiments may be described and/or claimed.

21 Claims, 6 Drawing Sheets

(51) Int. Cl.
  *A61B 5/117*   (2016.01)
  *A61B 5/00*    (2006.01)
  *A61B 5/04*    (2006.01)

(52) U.S. Cl.
  CPC ............ *A61B 5/117* (2013.01); *A61B 5/6824* (2013.01); *A61B 5/7203* (2013.01); *A61B 5/7221* (2013.01)

(56) References Cited

U.S. PATENT DOCUMENTS

| | | | |
|---|---|---|---|
| 2012/0116198 A1* | 5/2012 | Veen | A61B 5/04284 600/372 |
| 2016/0157781 A1* | 6/2016 | Baxi | A61B 5/6897 600/301 |
| 2016/0274621 A1* | 9/2016 | Meyer | B29C 39/021 |
| 2018/0146870 A1* | 5/2018 | Shemesh | A61B 5/02416 |

OTHER PUBLICATIONS

"Introducing the Nymi Band," <https://www.nymi.com/the-nymi-band/> [retrieved Oct. 9, 2015], 11 pages.
International Search Report and Written Opinion dated Aug. 11, 2016, issued in International Application No. PCT/US2016/031068, 13 pages.

* cited by examiner

USER'S PHYSIOLOGICAL CONTEXT SENSING METHOD AND APPARATUS

FIELD

Embodiments of the present disclosure generally relate to the field of sensor devices, and more particularly, to devices, such as wearable devices, configured to sense user's physiological context for various applications, such as biometric authentication.

BACKGROUND

With advances in various technologies, wearable sensing devices or systems are increasingly popular. A wearable sensing system may need to be comfortably attached to the human body, and may be able to measure and quantify various parameters of a user's physiological context, such as, for example, electrocardiogram (ECG), electromyogram (EMG), electroencephalogram (EEG), and the like, as well as provide user authentication based on biometric measurements, to enable "no password" device unlocking. However, the quality of a user's physiological context readings and performance of biometric authentication algorithms (e.g., based on ECG readings) are highly dependent on the quality and repeatability of signals (e.g., ECG signals) sensed from the human body. The quality of ECG signals is dependent on the electrode material and the electrode-tissue impedance (ETI). ETI levels may vary dependent on the level of dryness of the hands of the user. This difference in ETI may affect the quality and repeatability of ECG signals and in turn, the accuracy of measurements of the user's physiological context and biometric authentication.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Figure 1:
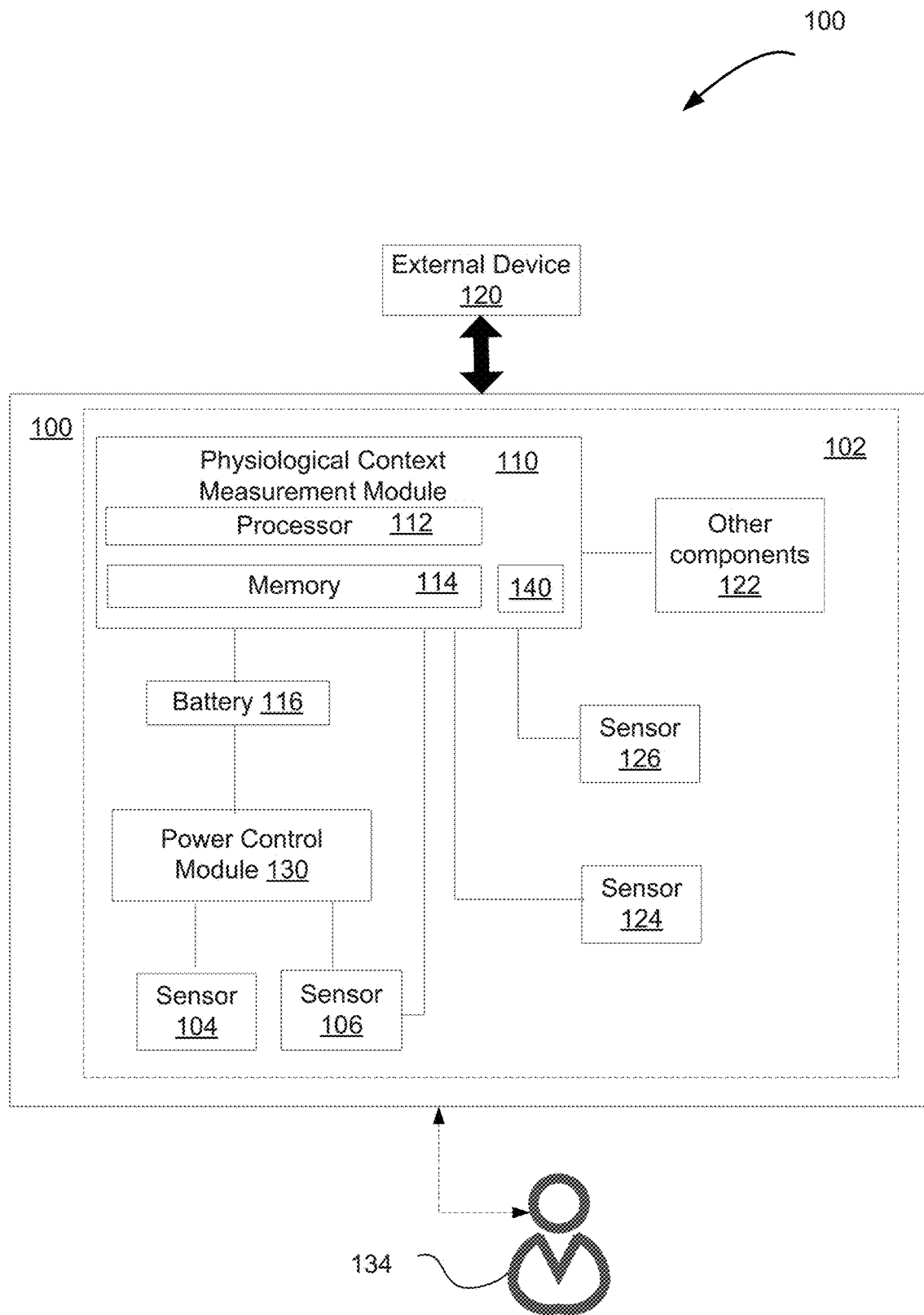
FIG. 1 is a block diagram illustrating an example apparatus incorporated with the physiological context sensing technology of the present disclosure, in accordance with some embodiments.

Embodiments of the present disclosure include techniques and configurations for an apparatus for a user's physiological context measurements. In accordance with embodiments, the apparatus may comprise a physiological context measurement module including first and second electrodes, to obtain one or more parameters of physiological context of a user in response to a provision of contact of the first and second electrodes with at least a portion of a body of the user while the physiological context measurement module is powered on. The apparatus may further comprise a third electrode coupled with the physiological context measurement module, wherein the physiological context measurement module may be powered on in response to detection of contact between the user's body portion and the third electrode. The first, second, and third electrodes may be disposed in the apparatus to facilitate simultaneous contact of the user's body portion with the first, second, and third electrodes, and to facilitate collection of the one or more parameters of the physiological context while the simultaneous contact is maintained. The apparatus may further include a fourth electrode coupled with the physiological context measurement module to provide a common reference signal for the first and second electrodes, wherein the physiological context measurement module may be powered in response to the detection of contact between the user's body portion and the third and fourth electrodes.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), (A) or (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

FIG. 1 is a block diagram illustrating an example apparatus 100 incorporated with the physiological context technology of the present disclosure, in accordance with some embodiments. The apparatus 100 may be a device, such as a wearable device, configured to be attachable to a user's body in order to conduct measurements associated with the functioning of the user's body and user's activities. In some embodiments, the apparatus 100 may comprise a mobile device, e.g., a tablet computer, a smartphone, a 1-in-2 computing device, or the like.

The apparatus 100 may include at least three or more sensors 104, 106, 124, 126. The sensors 124, 126 may be configured to monitor a process that is external to the apparatus 100. For example, in some embodiments, where the apparatus 100 comprises a wearable device, the sensors 124, 126 may provide readings of a user's physiological context, such as, data related to various user body functions. More specifically, the sensors 124, 126 may include, but may not be limited to, electrocardiogram (ECG) electrodes, electromyography (EMG) electrodes, electroencephalogram (EEG) electrodes, or the like. In embodiments, the sensors 124, 126 may further include temperature sensors, sweat chemical sensors, motion sensors, galvanic skin response (GSR) sensors, piezo crystals, pressure sensors, or the like. In some embodiments, the sensors 124, 126 may comprise capacitive electrodes configured to sense ECG data, for example. In embodiments, the apparatus 100 may be configured to biometrically authenticate the user based at least in part on the collected parameters of the physiological context of the user.

The apparatus 100 may further include sensors 104 and 106 coupled with the sensors (capacitive electrodes) 124, 126. At least one of the sensors (e.g., 104) may be configured to detect contact with the at least a portion of a user's body 134. Another sensor, e.g., 106 may be configured to provide a common reference signal for the sensors (capacitive electrodes) 124, 126. As will be described below in greater detail, sensor 106 may be further configured to inject current of a certain value into the user's body 134, to be detected by the sensor 104 in response to completion of the circuit via the user's body, to detect contact with at least a portion of the user's body 134.

The sensors 104, 106, 124, 126 may be disposed around a body 102 of the apparatus 100 in a particular arrangement, such as to provide a possibility for contact with at least a portion of a user's body 134. In embodiments, the body 102 may comprise a printed circuit board (PCB) disposed in the apparatus 100. For example, when the apparatus 100 comprises a wearable device, the sensors 104, 106, 124, 126 may be placed around the body 102 of the apparatus 100, to enable simultaneous contact with the user's body 134. For example, sensors 104, 106, and one of the sensors (capacitive electrodes) 124 or 126 may be placed on one side (e.g., outer surface) of the body 102 of the apparatus 100, in proximity to each other, to enable simultaneous contact with a portion of the user's body 134, such as an index finger, when the user puts her finger on the sensors 104, 106, and one of 124, 126. Another one of the sensors (capacitive electrodes) 124 or 126 may be placed on another, opposite side (e.g., inner surface) of the body 102 of the apparatus 100, to enable contact with the skin of the user's body 134. In another example, sensors 104, 106, 124, 126 may be placed on the same side of the body 102 of the apparatus 100, in proximity to each other, to enable simultaneous contact with a portion of the user's body 134. The disposition of the sensors 104, 106, 124, 126 around the body 102 of the apparatus 100 will be discussed in detail in reference to FIGS. 3-5.

It should be noted that sensors 104, 106, 124, 126 are shown in FIG. 1 for illustration only and are not limiting the implementation of apparatus 100. It will be appreciated that any number or types of sensors may be used in the apparatus 100.

In some embodiments, the apparatus 100 may include a physiological context measurement module 110 coupled with the sensors (capacitive electrodes) 124, 126, to obtain one or more parameters of physiological context of a user sensed by the sensors 124, 126. The physiological context measurement module 110 may include a processor 112 and memory 114 having instructions that, when executed on the processor 112, may cause the processor 112 to process readings of the user's physiological context provided by the sensors (capacitive electrodes) 124, 126. The physiological context measurement module 110 may further include module (e.g., circuitry) 140 configured to receive and pre-process readings provided by the sensors 124, 126, and provide pre-processed readings to the processor 112 for further processing. In general, the control module 130 may have hardware or software implementation, or a combination thereof. The components of the physiological context measurement module 110, such as circuitry 140, are described in greater detail in reference to FIG. 2.

The apparatus 100 may include a battery 116 configured to provide power supply to the apparatus 100 and, more generally, to the components of the apparatus 100, for example, to physiological context measurement module 110.

The apparatus 100 may include other components 122 necessary for the functioning of the apparatus 100. For example, other components 122 may include communications interface(s) to enable the apparatus 100 to communicate over one or more wired or wireless network(s) and/or with any other suitable device, such as external device 120 (e.g., mobile or stationary computing device). For example, the other components 122 may include a transmitter to transmit a communication signal provided by the apparatus 100 to different destinations, such as to external device 120. The other components 122 may be further configured to perform signal pre-processing before transmission of sensed signals via the transmitter, such as de-noising, feature extraction, classification, data compression, and the like.

To enable a user's physiological context measurements, the apparatus 100 may include a power control module 130 communicatively coupled with the sensors 104 and 106 and the battery 116, and configured to control the power supply provided by the battery 116 to the physiological context measurement module 110. The control module 130 may be configured to power on the physiological context measurement module 110 in response to detection of contact between a portion of the user's body 134 (e.g., a finger) and the sensor 104, or, in some embodiments, with the sensors 104 and 106. For example, sensor 104 may detect a contact with a portion of the user's body 134 and provide a corresponding signal to the power control module 130. The power control module 130, in response to a receipt of the signal, may issue a control signal to the battery 116 to power on the physiological context measurement module 110, to enable measurements and processing of the user's physiological context provided by the sensors 124, 126. An example implementation of the operation of the power management of the apparatus 100 will be described in greater detail in reference to FIG. 2.

Figure 2:
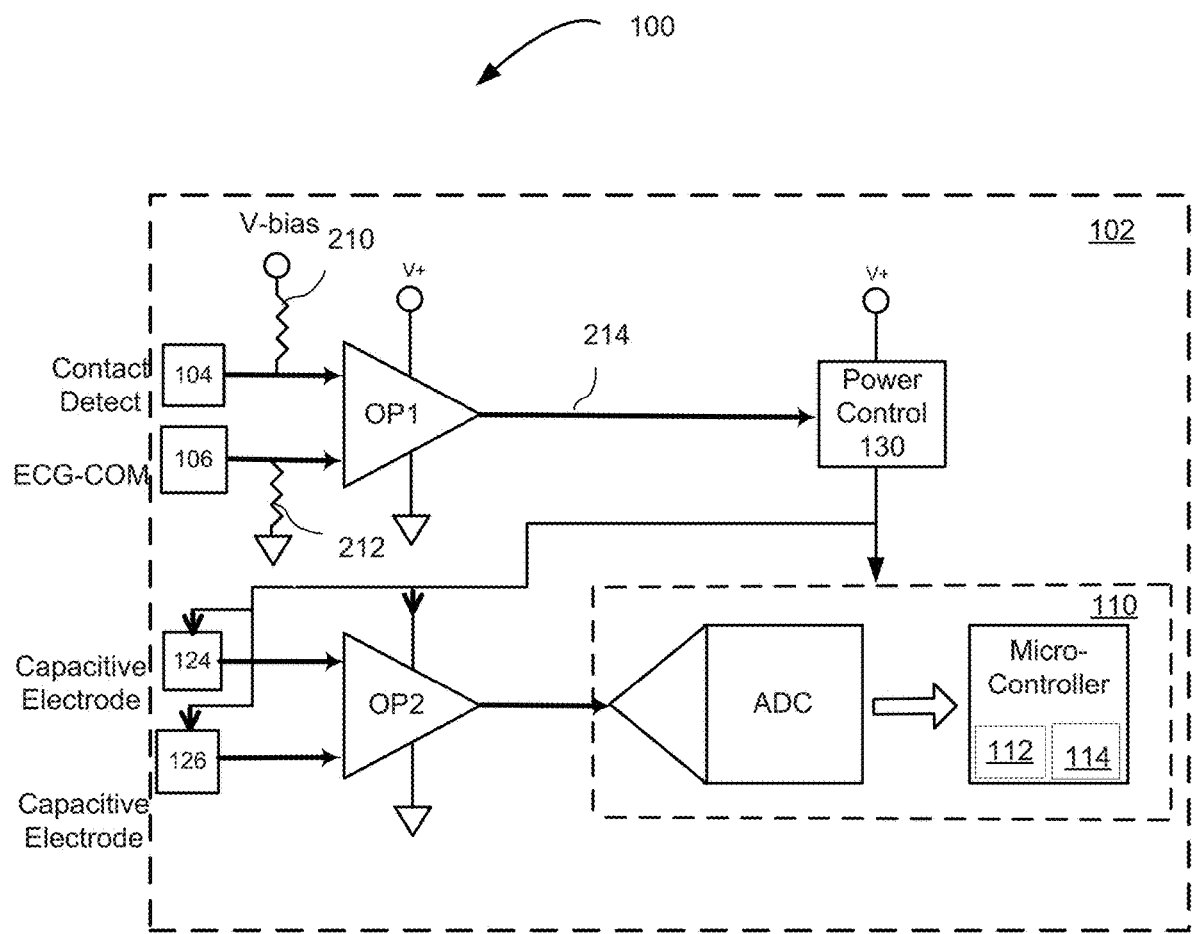
FIG. 2 is an example schematic diagram of an apparatus for providing a user's physiological context measurements, in accordance with some embodiments.

FIG. 2 is an example schematic diagram of an apparatus for providing a user's physiological context measurements, in accordance with some embodiments. More specifically, the schematic diagram of FIG. 2 may provide at least partial implementation of the components of the apparatus 100 of FIG. 1. For purposes of simplicity, like components of FIGS.

1 and 2 are indicated by like numerals. In embodiments, the apparatus 100 illustrated in FIG. 2 may comprise a wearable device.

The apparatus 100 may include two sensors (e.g., capacitive ECG electrodes) 124 and 126. As briefly described in reference to FIG. 1, the sensors 124, 126 may be mounted on opposite surfaces of the PCB 102. The PCB 102 may be attachably coupled with a strap (not shown) attachable to the user's body (e.g., to the wrist or any other part, such as chest, neck, foot, arm, forehead, or the like). For example, sensor 124 may be mounted on the upper surface of the PCB 102 and sensor 126 may be mounted on the lower surface of the PCB 102. Accordingly, sensor 126 may always be in contact with the user's body because it is located on the underside of the PCB 102, which may be in substantially permanent contact with the user's body (e.g., by virtue of being strapped onto the wrist). Sensors 124, 126 may be connected as inputs to a differential amplifier OP2. OP2 may be configured to amplify the resultant readings of the user's physiological context, such ECG signal, and feed the signal to the input of the physiological context measurement module 110. More specifically, the signal from OP2 may be input into an analog to digital converter ADC for digitization. The ADC may provide the digitized readings to a microcontroller comprising processor 112 and memory 114.

The apparatus 100 may further include sensors 104, 106 that may serve as contact detection electrodes. To measure the user's physiological context (e.g., ECG), the user may be required to place the finger of their hand on the PCB 102 to make simultaneous contact with sensors 104, 106, 124. Because sensors 124, 126 are active capacitive electrodes, they may consume power in standby state. Accordingly, the apparatus 100 may be configured to power gate sensors 124, 126, amplifier OP2, and the physiological context measurement module 110 and power them on when simultaneous contact with at least sensors 104, 106, and 124 (and, in some embodiments, with 126) is detected by the contact detection circuit formed by sensors 104, 106, differential amplifier OP1 and the associated biasing resistors 210 and 212, shown in FIG. 2. More specifically, on placement of the user's finger on the sensors 104, 106, and 124, the bias current through the resistors 210 and 212 at input of OP1 may change, in response to bias voltage provided by the V-bias voltage supply source, as shown. This current change may cause the differential amplifier OP1 to provide a corresponding signal 214 to the power control module 130, to trigger the power control module 130 to enable power (e.g., connect the battery 116, not shown in FIG. 2) to the physiological context measurement module 110, the sensors (capacitive electrodes) 124, 126, and differential amplifier OP2. Accordingly, sensors 124 and 126 may receive readings of the user's physiological context (e.g., ECG readings) and provide the readings to powered-on physiological context measurement module 110 for processing.

As soon as the finger is removed from the sensors 104, 106, and 124, the bias current of the differential amplifier OP1 may be restored to a nominal value, which may signal the power control module 130 to disable power supply to the sensors 124, 126, OP2, and physiological context measurement module 110. Additionally, electrode 106, which has an impedance path to ground below a threshold, may also serve as a common reference electrode (ECG-COM) for the capacitive electrodes 124 and 126, to reduce the common mode noise in the user's physiological context readings. Sensors 104 and 106 may be fabricated, for example, on a glass-epoxy substrate with gold plated copper contacts and separated by at least 1 mm distance, so as to avoid false triggering in humid environments. In embodiments, OP1, OP2, ADC, and resistor 210 and 212 may comprise circuitry 140 of FIG. 1.

Figure 3:
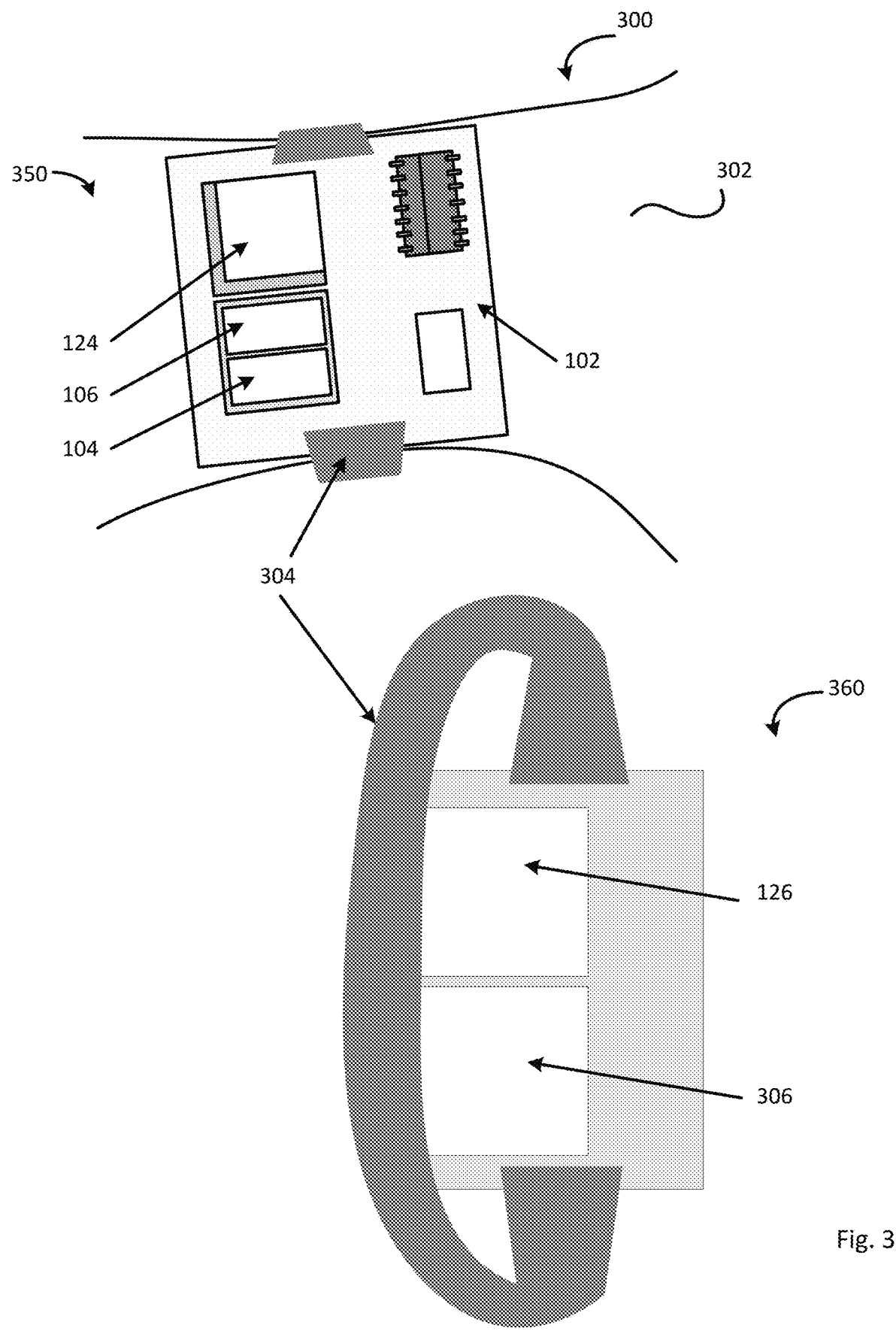
FIGS. 3-4 illustrate different views of an example apparatus of FIGS. 1-2 comprising a wearable device for providing a user's physiological context measurements, removably attachable to a user's wrist, in accordance with some embodiments.
Figure 4:
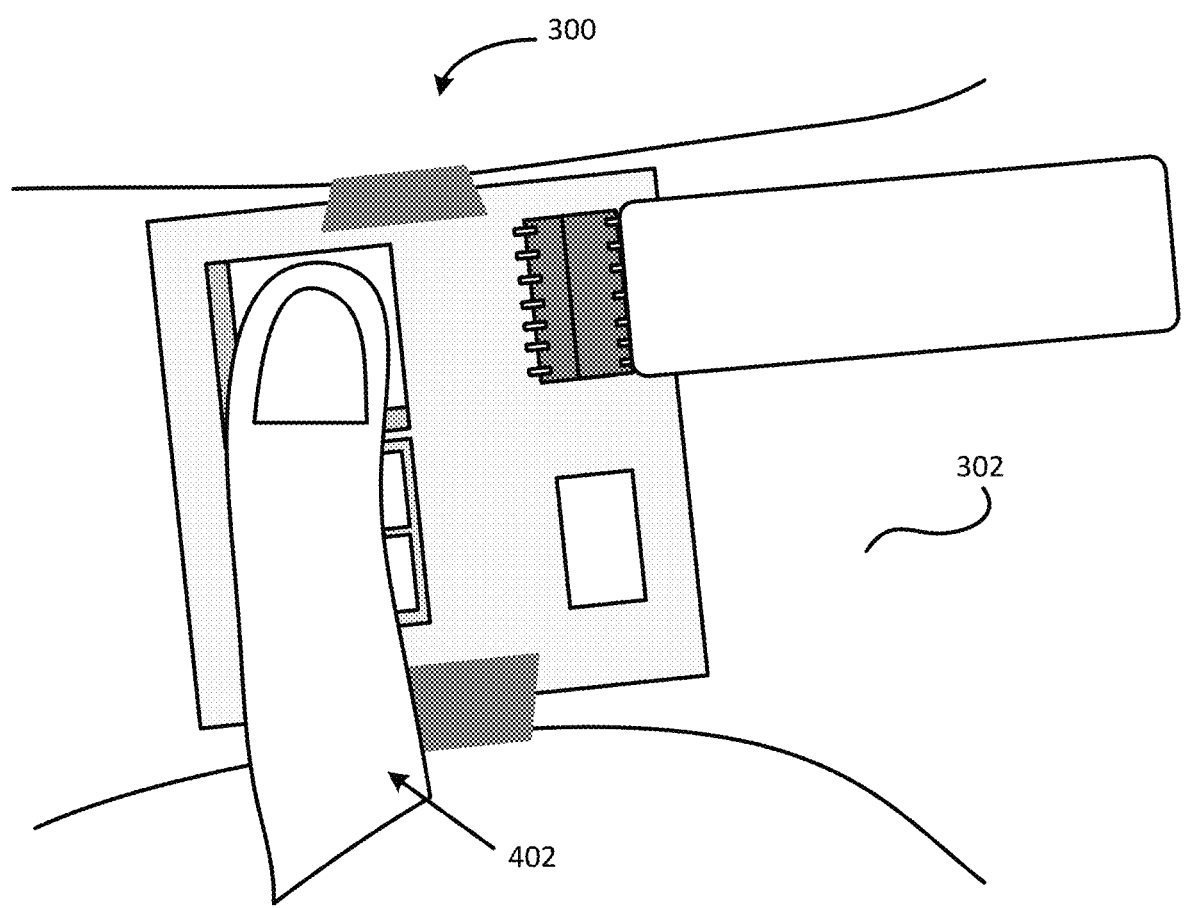

FIGS. 3-4 illustrate different views of an example apparatus of FIGS. 1-2 comprising a wearable device for providing a user's physiological context measurements, removably attachable to a user's wrist, in accordance with some embodiments.

FIG. 3 illustrates a top view 350 and a bottom view 360 of a wearable device 300 removably attachable to the user's wrist, in accordance with some embodiments. The views 350 and 360 may include the components of the apparatus 100. As shown, the wearable device 300 may comprise a PCB 102 housing the components of apparatus 100 and disposed on a wrist band 304, attachable to the user's wrist 302. More specifically, the PCB 102 is shown as housing the capacitive sensor 124 and contact detection sensors 104, 106 on the top (outer) surface of the PCB 102, and the capacitive sensor 126 on the bottom (inner) surface of the PCB 102, to provide substantially simultaneous contact for the user's finger with sensors 104, 106, 124 (if placed on these sensors), and substantially permanent contact of the sensor 126 with the user's wrist 302 (when device 300 is placed on the user's wrist 302), to complete the circuit formed by the user's finger and the sensors 104, 106, 124 via the user's body, in response to a placement of the finger on the sensors 104, 106, 124. As shown, the sensors 104, 106, 124 are placed on the PCB 102 in proximity to each other, to facilitate simultaneous contact with the user's finger. A dummy sensor shell 306 may be disposed on the inner surface of the PCB 102, opposite the sensors 104, 106, as shown.

It will be understood that the wristband implementation of the apparatus 100 is described for illustration only. In general, the apparatus for the user's physiological context described herein may be implemented as a biometric wearable device, a smart watch, or a mobile computing device. The apparatus may include a wearable knee strap, a wearable chest strap, a wearable neck strap, a wearable wrist strap, or a wearable foot strap and be used in connection with knee bands, ankle caps, vests, garments, or the like. In principle, apparatus 100 may be applied to any human joint or body part, such as a knee, arm, neck, chest, forehead, or the like.

FIG. 4 illustrates the wearable device of FIG. 3 in operation, in accordance with some embodiments. As shown, the wearable device 300 is placed on the user's wrist 302. The user may enable the measurements of his or her physiological context by the device 300 by placing index finger 402 of his or her other hand on top-side sensors (electrodes) 104, 106, 124 (not shown in FIG. 4) to ensure simultaneous contact with these electrodes. As discussed above, the provision of simultaneous contact with the sensors 104, 106, 124 enables powering on the sensors 104, 106, and the physiological context measurement module 110, and the measurements of the user's physiological context may commence by the capacitive electrodes 124, 126 (not shown in FIG. 4) taking the readings from the user's index finger 402.

A wearable device implemented as described above may provide a number of advantages compared to conventional wearable sensor device solutions configured to measure a user's physiological context. For example, using capacitive electrodes instead of conventional metal ones (e.g., for ECG sensing) may help reduce the adverse impact of dryness of hands on ECG measurements quality. Accordingly, ECG signal quality may improve even with different dryness levels of hands across an individual user and across a group of users using the wearable device described above. Better and more reliable ECG signal quality is an important factor in reducing equal error rate, thereby making wrist-based ECG-based authentication more robust.

To improve performance of capacitive electrodes (124, 126 of FIG. 1) that may be susceptible to noise pickup (due to their high internal impedance and large capacitance), a third electrode (e.g., 106) may be used as a virtual ground reference electrode to improve common mode rejection ratio (CMRR) of the readings sensed by capacitive electrodes. Utilizing a pair of capacitive electrodes, in conjunction with a reference ground electrode, may result in better measurement (e.g., ECG) signal quality due to lesser baseline wandering, lesser low-frequency artifacts and reduced 50/60 Hz mains interference.

The user's physiological context measurement circuits (e.g., electrodes 124, 126, OP2, and physiological context measurement module 110 as described in reference to FIG. 2) may be power gated to reduce standby power consumption. That is, the circuits and module 110 may be powered on in response to a detection of the user's body portion (e.g., a finger) simultaneously touching both electrode sets (e.g., 104-106 and 124-26). The four-electrode design may enable a more robust measurement signal (e.g., ECG signal) quality and repeatability, for example, in a wrist worn form factor described in reference to FIGS. 3-4, compared to the conventional designs utilizing two or three dry metallic electrodes.

Figure 5:
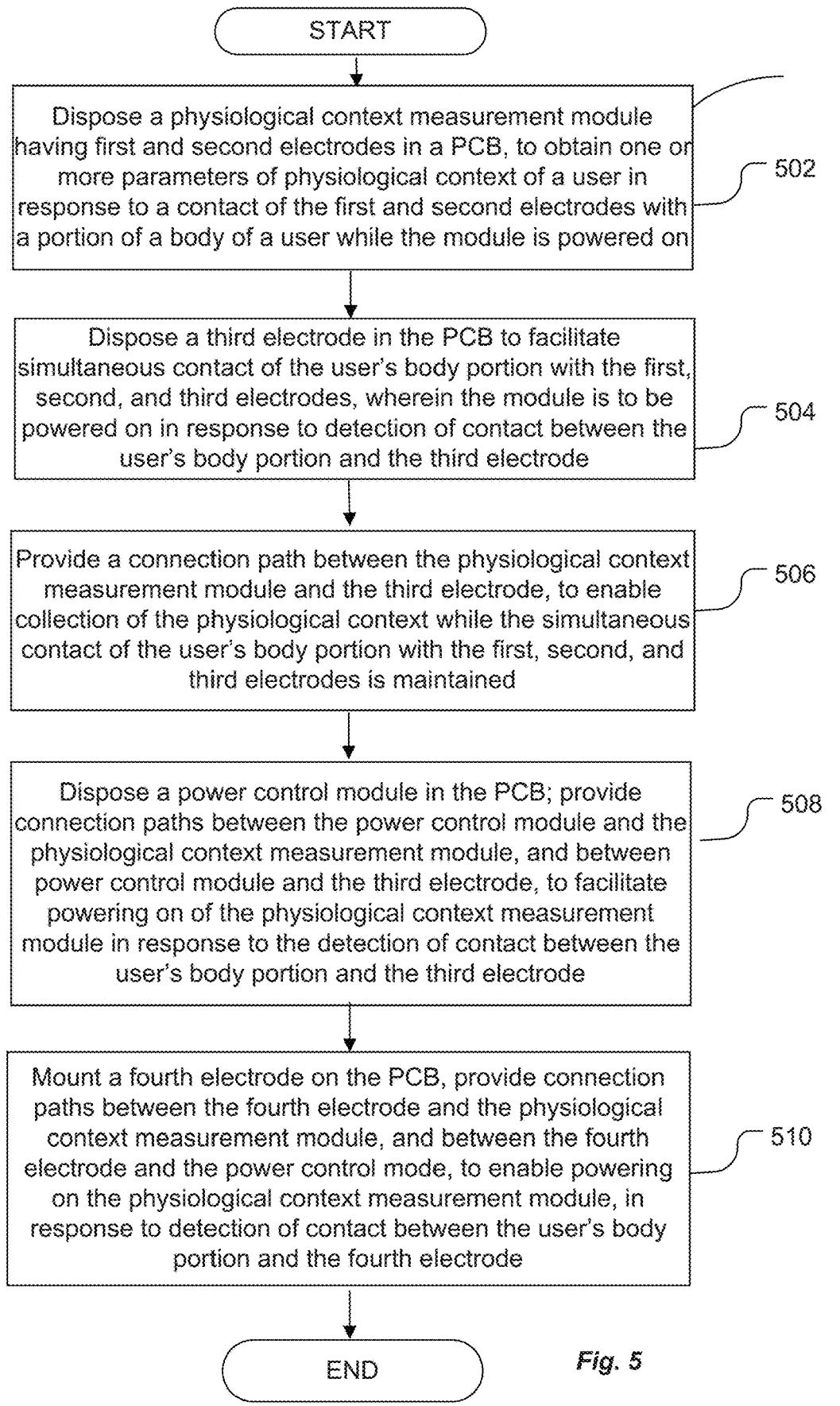
FIG. 5 is a process flow diagram for assembling a wearable apparatus for providing a user's physiological context measurements, in accordance with some embodiments.

FIG. 5 is a process flow diagram for assembling a wearable apparatus for providing a user's physiological context measurement, in accordance with some embodiments. The process 500 may comport with some of the apparatus embodiments described in reference to FIGS. 1-4. In alternate embodiments, the process 500 may be practiced with more or less operations, or a different order of the operations.

The process 500 may begin at block 502 and include disposing a physiological context measurement module having first and second electrodes in a PCB, to obtain one or more parameters of physiological context of a user in response to a contact of the first and second electrodes with at least a portion of a body of a user of the wearable device while the physiological context measurement module is powered on.

At block 504, the process 500 may include disposing a third electrode in the PCB to facilitate simultaneous contact of the user's body portion with the first, second, and third electrodes, wherein the physiological context measurement module is to be powered on in response to detection of contact between the user's body portion and the third electrode.

At block 506, the process 500 may include providing a connection path between the physiological context measurement module and the third electrode, to enable collection of the one or more parameters of the physiological context while the simultaneous contact of the user's body portion with the first, second, and third electrodes is maintained.

At block 508, the process 500 may include disposing a power control module in the PCB; providing a connection path between the power control module and the physiological context measurement module; and providing a connection path between the power control module and the third electrode, to facilitate powering on of the physiological context measurement module, wherein the power control module is to power on the physiological context measurement module in response to the detection of contact between the user's body portion and the third electrode.

At block 510, the process 500 may include mounting a fourth electrode on the PCB, providing a connection path between the fourth electrode and the physiological context measurement module, to provide a common reference signal for the first and second electrodes, and providing a connection path between the fourth electrode and the power control module, to enable powering on, by the power control module, the physiological context measurement module, in response to detection of contact between the user's body portion and the fourth electrode. The fourth electrode may be disposed in proximity to the first, second, and third electrodes, to enable simultaneous contact of the user's body portion with the first, second, third, and fourth electrodes. The first, third, and fourth electrodes may be on a first surface of the PCB; and the second electrode may be disposed on the first surface of the PCB or on a second surface of the PCB, opposite the first surface.

Figure 6:
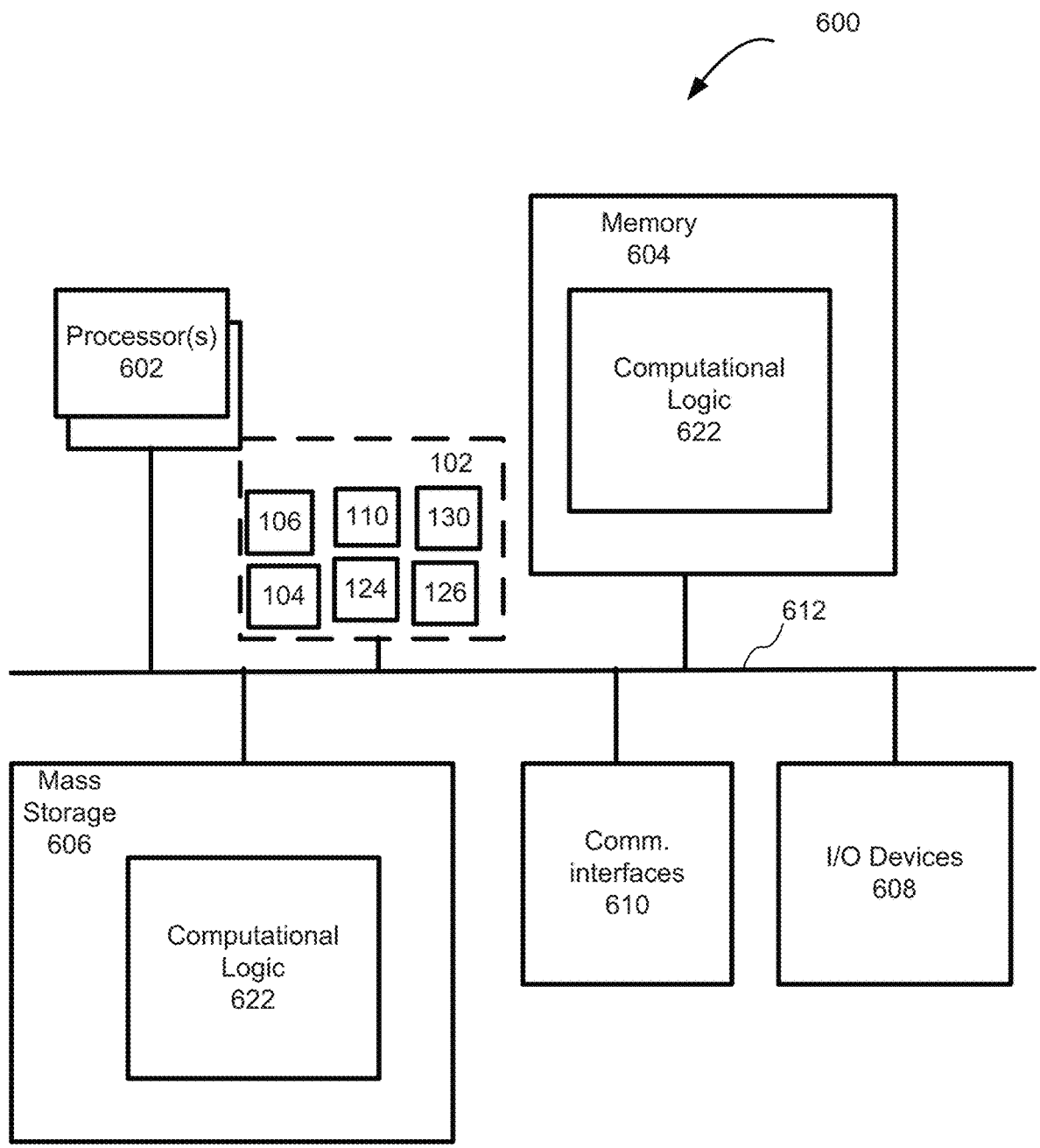
FIG. 6 illustrates an example computing device suitable for use with various components of FIGS. 1-4, such as an apparatus for providing a user's physiological context measurements, in accordance with various embodiments.

FIG. 6 illustrates an example computing device 600 suitable for use with various components of FIGS. 1-4, such as an apparatus for providing a user's physiological context measurements, in accordance with various embodiments. In some embodiments, various components of the example computing device 600 may be used to configure the apparatus 100 or wearable device 300. In some embodiments, various components of the example computing device 600 may be used to configure the external device 120. As shown, computing device 600 may include one or more processors or processor cores 602 and system memory 604. For the purpose of this application, including the claims, the terms "processor" and "processor cores" may be considered synonymous, unless the context clearly requires otherwise. The processor 602 may include any type of processors, such as a central processing unit (CPU), a microprocessor, and the like. The processor 602 may be implemented as an integrated circuit having multi-cores, e.g., a multi-core microprocessor. The computing device 600 may include mass storage devices 606 (such as solid state drives, volatile memory (e.g., dynamic random-access memory (DRAM)), and so forth). In general, system memory 604 and/or mass storage devices 606 may be temporal and/or persistent storage of any type, including, but not limited to, volatile and non-volatile memory, optical, magnetic, and/or solid state mass storage, and so forth. Volatile memory may include, but is not limited to, static and/or dynamic random-access memory. Non-volatile memory may include, but is not limited to, electrically erasable programmable read-only memory, phase change memory, resistive memory, and so forth. System memory 604 and/or mass storage devices 606 may include respective copies of programming instructions configured to perform operations related to apparatus 100, for example, collectively denoted as computational logic 622.

The computing device 600 may further include input/output (I/O) devices 608 (such as a display, soft keyboard, touch sensitive screen, image capture device, and so forth) and communication interfaces 610 (such as network interface cards, modems, infrared receivers, radio receivers (e.g., Near Field Communication (NFC), Bluetooth, WiFi, 4G/5G Long-Term Evolution (LTE)), and so forth).

The communication interfaces 610 may include communication chips (not shown) that may be configured to operate the device 600 in accordance with a Global System for Mobile Communication (GSM), General Packet Radio Service (GPRS), Universal Mobile Telecommunications System (UMTS), High Speed Packet Access (HSPA), Evolved HSPA (E-HSPA), or LTE network. The communication chips may also be configured to operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chips may be configured to operate in accordance with Code Division Multiple Access (CDMA), Time Division Multiple Access (TDMA), Digital Enhanced Cordless Telecommunications (DECT), Evolution-Data Optimized (EV-DO), derivatives thereof, as well as any other wireless protocols that are designated as 3G, 4G, 5G, and beyond. The communication interfaces 610 may operate in accordance with other wireless protocols in other embodiments.

In embodiments, the computing device 600 may comprise the apparatus 100 of FIGS. 1-2 or device 300 of FIGS. 3-4. In some embodiments, the device 600 may include sensors 104, 106, 124, 126, and components of physiological context module 110 and power control module 130 disposed in PCB 102 as described herein.

The above-described computing device 600 elements may be coupled to each other via system bus 612, which may represent one or more buses. In the case of multiple buses, they may be bridged by one or more bus bridges (not shown). Each of these elements may perform its conventional functions known in the art. In particular, system memory 604 and mass storage devices 606 may be employed to store a working copy and a permanent copy of the programming instructions implementing the operations associated with the apparatus 100 of FIG. 1. The various elements may be implemented by assembler instructions supported by processor(s) 602 or high-level languages that may be compiled into such instructions.

The permanent copy of the programming instructions of computational logic 622 may be placed into permanent storage devices 606 in the factory, or in the field, through, for example, a distribution medium (not shown), such as a compact disc (CD), or through communication interfaces 610 (from a distribution server (not shown)). That is, one or more non-transitory distribution media having an implementation of the agent program may be employed to distribute the agent and to program various computing devices. In embodiments, the distribution media may be transitory, e.g., signals encoded with the instructions.

The number, capability, and/or capacity of the elements 608, 610, 612 may vary, depending on whether computing device 600 is used as a stationary computing device, such as a set-top box or desktop computer, or a mobile computing device, such as a tablet computing device, laptop computer, game console, or smartphone. Their constitutions are otherwise known, and accordingly will not be further described.

At least one of processors 602 may be packaged together with memory having computational logic 622 configured to practice aspects of embodiments described in reference to FIGS. 1-4. For one embodiment, at least one of processors 602 may be packaged together with memory having computational logic 622 to form a System in Package (SiP) or a System on Chip (SoC). For at least one embodiment, the SoC may be utilized in, e.g., but not limited to, a computing device, such as external device 120 of FIG. 1. In another embodiment, the SoC may be utilized to form the physiological context measurement module 110 of FIG. 1.

In various implementations, the computing device 600 may comprise a mobile device, a wearable device, a laptop, a netbook, a notebook, an ultrabook, a smartphone, a tablet, a personal digital assistant (PDA), or an ultra mobile PC. In further implementations, the computing device 600 may be any other electronic device that processes data.

Example 1 is an apparatus, comprising a physiological context measurement module including first and second electrodes, to obtain one or more parameters of physiological context of a user in response to a provision of contact of the first and second electrodes with at least a portion of the body of the user while the physiological context measurement module is powered on; and a third electrode coupled with the physiological context measurement module, wherein the physiological context measurement module is to be powered on in response to detection of contact between the user's body portion and the third electrode, wherein the first, second, and third electrodes are disposed in the apparatus to facilitate simultaneous contact of the user's body portion with the first, second, and third electrodes, and collection of the one or more parameters of the physiological context while the simultaneous contact is maintained.

Example 2 may include the subject matter of Example 1, further comprising: a power control module coupled with the physiological context measurement module and the third electrode, wherein the power control module is to power on the physiological context measurement module in response to the detection of contact between the user's body portion and the third electrode.

Example 3 may include the subject matter of Example 2, further comprising: a fourth electrode coupled with the physiological context measurement module to provide a common reference signal for the first and second electrodes, wherein the power control module is to further power on the physiological context measurement module in response to detection of contact between the user's body portion and the fourth electrode.

Example 4 may include the subject matter of Example 3, wherein the first and second electrodes are capacitive electrodes, wherein the fourth electrode has impedance to ground that is below a threshold.

Example 5 may include the subject matter of Example 3, wherein the fourth electrode is further coupled to the power control module, wherein the power control module is to power on the physiological context measurement module in response to detection of contact between the user's body portion and the fourth electrode.

Example 6 may include the subject matter of Example 5, wherein the fourth electrode is disposed in the apparatus to enable simultaneous contact of the user's body portion with the first, second, third and fourth electrodes.

Example 7 may include the subject matter of Example 6, wherein the first, third, and fourth electrodes are disposed on a first surface of the apparatus.

Example 8 may include the subject matter of Example 7, wherein the second electrode is disposed on the first surface of the apparatus or on a second surface of the apparatus, opposite the first surface.

Example 9 may include the subject matter of Example 8, further comprising a printed circuit board (PCB), wherein the first and second surfaces comprise respective surfaces of the PCB, and wherein the physiological context measurement module and power control module are disposed in the PCB.

Example 10 may include the subject matter of Example 9, wherein the apparatus further includes: a first differential amplifier coupled to the third and fourth electrodes, wherein the third and fourth electrodes are coupled with first and second resistors respectively at an input of the first differential amplifier, wherein bias current of the differential amplifier passing through the first and second resistors is to change in response to the simultaneous contact; and wherein the power control module is coupled with the first differential amplifier, to receive a signal outputted by the differential amplifier in response to a change of the bias current, and to provide an output signal to power on the physiological context measurement module.

Example 11 may include the subject matter of Example 10, wherein the physiological context measurement module further includes: a second differential amplifier coupled with the first and second electrodes, to receive readings of the one or more parameters of the user' physiological context; an analog to digital controller (ADC) coupled with the second differential amplifier, to receive amplified readings of the one or more parameters provided by the second differential amplifier and to digitize the amplified readings; and a processing unit coupled with the ADC, to receive and process the digitized readings.

Example 12 may include the subject matter of Example 11, wherein the third and fourth electrodes comprise a metal disposed on a glass epoxy substrate.

Example 13 may include the subject matter of Example 12, wherein the physiological context is selected from one of: electrocardiogram (ECG), electromyogram (EMG), or electroencephalogram (EEG), wherein the apparatus is to biometrically authenticate the user based at least in part on the collected one or more parameters of the physiological context of the user.

Example 14 may include the subject matter of Example 13, wherein the physiological context is ECG, and wherein the user's body portion is a finger.

Example 15 may include the subject matter of any of Examples 1 to 14, wherein the apparatus is a wearable device, wherein the wearable device comprises a wearable knee strap, a wearable chest strap, a wearable neck strap, a wearable wrist strap, or a wearable foot strap.

Example 16 is a wearable device, comprising: a printed circuit board (PCB), including: a physiological context measurement module including first and second capacitive electrodes to obtain one or more parameters of physiological context of a user in response to a provision of contact of the first and second electrodes with at least a portion of the body of the user while the physiological context measurement module is powered on; and a third electrode coupled with the physiological context measurement module, wherein the physiological context measurement module is to be powered on in response to detection of contact between the user's body portion and the third electrode, wherein the first and second capacitive electrodes and the third electrode are disposed in the PCB to facilitate simultaneous contact of the user's body portion with the first and second capacitive electrodes and the third electrode, and collection of the one or more parameters of the physiological context while the simultaneous contact is maintained.

Example 17 may include the subject matter of Example 16, wherein the PCB further includes: a power control module coupled with the physiological context measurement module and the third electrode, wherein the power control module is to power on the physiological context measurement module in response to the detection of contact between the user's body portion and the third electrode.

Example 18 may include the subject matter of Example 17, wherein the PCB further includes: a fourth electrode coupled with the physiological context measurement module to provide a common reference signal for the first and second capacitive electrodes, wherein the fourth electrode has impedance to ground that is below a threshold, and wherein the fourth electrode is further coupled to the power control module, wherein the power control module is to power on the physiological context measurement module in response to detection of contact between the user's body portion and the fourth electrode.

Example 19 may include the subject matter of Example 18, wherein the fourth electrode is disposed on the PCB to enable simultaneous contact of the user's body portion with the first, second, third, and fourth electrodes.

Example 20 may include the subject matter of any of Examples 16 to 19, further comprising a strap, wherein the PCB is attachably coupled with the strap, wherein the wearable system is selected from one of: a biometric wearable device, a smart watch, or a mobile computing device.

Example 21 is a method of fabricating a wearable device, comprising: disposing a physiological context measurement module having first and second electrodes in a printed circuit board (PCB), to obtain one or more parameters of physiological context of a user in response to a contact of the first and second electrodes with at least a portion of a body of a user of the wearable device while the physiological context measurement module is powered on; disposing a third electrode in the PCB to facilitate simultaneous contact of the user's body portion with the first, second, and third electrodes, wherein the physiological context measurement module is to be powered on in response to detection of contact between the user's body portion and the third electrode; and providing a connection path between the physiological context measurement module and the third electrode, to enable collection of the one or more parameters of the physiological context while the simultaneous contact of the user's body portion with the first, second, and third electrodes is maintained.

Example 22 may include the subject matter of Example 21, further comprising: disposing a power control module in the PCB; providing a connection path between the power control module and the physiological context measurement module; and providing a connection path between the power control module and the third electrode, to facilitate powering on of the physiological context measurement module, wherein the power control module is to power on the physiological context measurement module in response to the detection of contact between the user's body portion and the third electrode.

Example 23 may include the subject matter of Example 22, further comprising: mounting a fourth electrode on the PCB; providing a connection path between the fourth electrode and the physiological context measurement module, to provide a common reference signal for the first and second electrodes; providing a connection path between the fourth electrode and the power control module, to enable powering on, by the power control module, the physiological context measurement module, in response to detection of contact between the user's body portion and the fourth electrode.

Example 24 may include the subject matter of Example 23, wherein mounting a fourth electrode on the PCB includes disposing the fourth electrode in proximity to the first, second, and third electrodes, to enable simultaneous contact of the user's body portion with the first, second, third, and fourth electrodes.

Example 25 may include the subject matter of Example 24, wherein mounting first, second, third, and fourth electrodes on the PCB includes: disposing the first, third, and fourth electrodes on a first surface of the PCB; and disposing the second electrode on the first surface of the PCB or on a second surface of the PCB, opposite the first surface.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. An apparatus, comprising:
   a physiological context measurement module including first and second electrodes, to obtain one or more parameters of physiological context of a user in response to a provision of contact of the first and second electrodes with a body of the user while the physiological context measurement module is powered on;
   a third electrode coupled with the physiological context measurement module, to detect contact between a first portion of the user's body and the third electrode; and
   a fourth electrode coupled with the physiological context measurement module, to provide a common reference signal for the first and second electrodes, wherein the physiological context measurement module is to be powered on in response to the detection of contact between the user's first body portion and the third electrode, wherein the first, third, and fourth electrodes are disposed on a first surface of the apparatus that comprises an outer surface of a body of the apparatus, to provide simultaneous contact of the user's first body portion with the first, third, and fourth electrodes, wherein the second electrode is disposed on a second surface of the apparatus that is opposite the first surface and comprises an inner surface of the apparatus body, to provide contact of a second body portion of the user with the second electrode, and to facilitate collection of the one or more parameters of the physiological context while a simultaneous contact between the first and second portions of the user's body and the first and second electrodes respectively is maintained.

2. The apparatus of claim 1, further comprising: a power control module coupled with the physiological context measurement module and the third electrode, wherein the power control module is to power on the physiological context measurement module in response to the detection of contact between the user's body portion and the third electrode.

3. The apparatus of claim 2, wherein the power control module is to further power on the physiological context measurement module in response to detection of contact between the user's first body portion and the fourth electrode.

4. The apparatus of claim 1, wherein the first and second electrodes are capacitive electrodes, wherein the fourth electrode has impedance to ground that is below a threshold.

5. The apparatus of claim 3, wherein the fourth electrode is further coupled to the power control module, wherein the power control module is to power on the physiological context measurement module in response to detection of contact between the user's first body portion and the fourth electrode.

6. The apparatus of claim 1, wherein the fourth electrode is disposed in the apparatus to enable simultaneous contact of the user's body with the first, second, third and fourth electrodes.

7. The apparatus of claim 5, further comprising a printed circuit board (PCB), wherein the first and second surfaces comprise respective surfaces of the PCB, and wherein the physiological context measurement module and power control module are disposed in the PCB.

8. The apparatus of claim 7, wherein the apparatus further includes:
   a first differential amplifier coupled to the third and fourth electrodes, wherein the third and fourth electrodes are coupled with first and second resistors respectively at an input of the first differential amplifier, wherein bias current of the differential amplifier passing through the first and second resistors is to change in response to the simultaneous contact of the second body portion with the first, third, and fourth electrodes; and
   wherein the power control module is coupled with the first differential amplifier, to receive a signal outputted by the differential amplifier in response to a change of the bias current, and to provide an output signal to power on the physiological context measurement module.

9. The apparatus of claim 8, wherein the physiological context measurement module further includes:
   a second differential amplifier coupled with the first and second electrodes, to receive readings of the one or more parameters of the user's physiological context;
   an analog to digital controller (ADC) coupled with the second differential amplifier, to receive amplified readings of the one or more parameters provided by the second differential amplifier and to digitize the amplified readings; and
   a processing unit coupled with the ADC, to receive and process the digitized readings.

10. The apparatus of claim 9, wherein the third and fourth electrodes comprise a metal disposed on a glass epoxy substrate.

11. The apparatus of claim 10, wherein the physiological context is selected from one of: electrocardiogram (ECG), electromyogram (EMG), or electroencephalogram (EEG), wherein the apparatus is to biometrically authenticate the user based at least in part on the collected one or more parameters of the physiological context of the user.

12. The apparatus of claim 11, wherein the physiological context is ECG, and wherein the user's first body portion is a finger.

13. The apparatus of claim 1, wherein the apparatus is a wearable device, wherein the wearable device comprises a wearable knee strap, a wearable chest strap, a wearable neck strap, a wearable wrist strap, or a wearable foot strap.

14. A wearable device, comprising:
   a printed circuit board (PCB), including:
      a physiological context measurement module including first and second capacitive electrodes to obtain one or more parameters of physiological context of a user in response to a provision of contact of the first and second capacitive electrodes with a body of the user while the physiological context measurement module is powered on;

a third electrode coupled with the physiological context measurement module, to detect contact between a first portion of the user's body and the third electrode; and a fourth electrode coupled with the physiological context measurement module, to provide a common reference signal for the first and second capacitive electrodes, wherein the physiological context measurement module is to be powered on in response to the detection of contact between the user's first body portion and the third electrode, wherein the first capacitive electrode, the third electrode, and the fourth electrode are disposed on a first side of the PCB that comprises an outer surface of a body of the wearable device, to facilitate simultaneous contact of the first user's body portion with the first capacitive electrode, and the third and fourth electrodes, and wherein the second capacitive electrode is disposed on a second side of the PCB that is opposite the first surface and comprises an inner surface of the wearable device body, to provide contact between a second body portion of the user and the second electrode, to facilitate collection of the one or more parameters of the physiological context while a simultaneous contact between the first and second portions of the user's body and the first and second capacitive electrodes respectively is maintained.

15. The wearable device of claim 14, wherein the PCB further includes:
a power control module coupled with the physiological context measurement module and the third electrode, wherein the power control module is to power on the physiological context measurement module in response to the detection of contact between the user's first body portion and the third electrode.

16. The wearable device of claim 15, wherein the fourth electrode has impedance to ground that is below a threshold, and
wherein the fourth electrode is further coupled to the power control module, wherein the power control module is to power on the physiological context measurement module in response to detection of contact between the user's first body portion and the fourth electrode.

17. The wearable device of claim 16, wherein the fourth electrode is disposed on the PCB to enable simultaneous contact of the user's first body portion with the first, second, third, and fourth electrodes.

18. The wearable device of claim 14, further comprising a strap, wherein the PCB is attachably coupled with the strap, wherein the wearable system is selected from one of: a biometric wearable device, a smart watch, or a mobile computing device.

19. A method of fabricating a wearable device, comprising:
disposing a physiological context measurement module having first and second electrodes in a printed circuit board (PCB), to obtain one or more parameters of physiological context of a user in response to a contact of the first and second electrodes with a body of a user of the wearable device while the physiological context measurement module is powered on, including disposing the first electrode on a first surface of the PCB that comprises an outer surface of a body of the wearable device, to provide contact between a first portion of the user's body and the first electrode, and disposing the second electrode on a second surface of the PCB that comprises an inner surface of the wearable device body, and is provided opposite the first surface, to provide contact between a second portion of the user's body and the second electrode;

disposing a third electrode on the first surface of the PCB to detect contact between the first portion of the user's body and the third electrode;

disposing a fourth electrode on the first surface of the PCB, to provide a common reference signal for the first and second electrodes, wherein the physiological context measurement module is to be powered on in response to a detection of contact between the first user's body portion and the third electrode; and providing a connection path between the physiological context measurement module and the third and fourth electrodes, to enable collection of the one or more parameters of the physiological context while a simultaneous contact of the first and second portions of the user's body with the first and second electrodes respectively is maintained.

20. The method of claim 19, further comprising:
disposing a power control module in the PCB;
providing a connection path between the power control module and the physiological context measurement module; and
providing a connection path between the power control module and the third electrode, to facilitate powering on of the physiological context measurement module, wherein the power control module is to power on the physiological context measurement module in response to the detection of contact between the user's first body portion and the third electrode.

21. The method of claim 20, further comprising:
providing a connection path between the fourth electrode and the power control module, to enable powering on, by the power control module, the physiological context measurement module, in response to detection of contact between the user's first body portion and the fourth electrode.

* * * * *